United States Patent [19]

Kigasawa et al.

[11] Patent Number: 4,528,372
[45] Date of Patent: Jul. 9, 1985

[54] N-PHTHALIDYL-5-FLUOROURACILS

[75] Inventors: Kazuo Kigasawa; Mineharu Hiiragi; Kikuo Wakisaka; Keiko Ichikawa, all of Tokyo; Kikuo Nakazato, Kanagawa; Taiji Okada, Hiroshima, all of Japan

[73] Assignee: Grelan Pharmaceutical Co., Ltd., Tokyo, Japan

[21] Appl. No.: 385,379

[22] PCT Filed: Sep. 30, 1981

[86] PCT No.: PCT/JP81/00260

§ 371 Date: May 21, 1982

§ 102(e) Date: May 21, 1982

[87] PCT Pub. No.: WO82/01370

PCT Pub. Date: Apr. 29, 1982

[30] Foreign Application Priority Data

Oct. 9, 1980 [JP] Japan ................. 55-140509

[51] Int. Cl.³ ................. C07D 405/04; A61K 31/505
[52] U.S. Cl. ................. 544/310
[58] Field of Search ................. 544/310

[56] References Cited

U.S. PATENT DOCUMENTS 2,997,481  8/1961  Wheeler ................. 549/303
3,971,784  7/1976  Tada ................. 544/310
4,196,202  4/1980  Okada ................. 544/313

FOREIGN PATENT DOCUMENTS 57-16881  1/1982  Japan ................. 544/310
57-32270  2/1982  Japan ................. 544/310
57-32271  2/1982  Japan ................. 544/310

OTHER PUBLICATIONS

Shionogi, *Chemical Abstracts* 98: 191755f (1983).
Grelan Pharm., *Chemical Abstracts* 99: 200538n (1983).
Grelan Pharm., *Chemical Abstracts* 100: 34560f (1984).
Banyu Pharm., *Chemical Abstracts* 100: 191904p (1984).

*Primary Examiner*—Donald G. Daus
*Assistant Examiner*—Stephen Kapner
*Attorney, Agent, or Firm*—Antonelli, Terry & Wands

[57] ABSTRACT

The present invention relates to novel N-phthalidyl-5-fluorouracil derivatives represented by the general formula

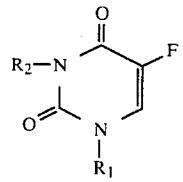

wherein one of $R_1$ and $R_2$ represents phthalidyl group

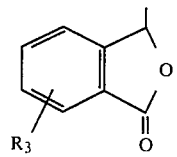

(wherein $R_3$ is a hydrogen atom, a halogen atom or a group selected from alkoxyl groups or alkyl groups) and the other represents a hydrogen atom, an acyl group or a cyclic ether group;

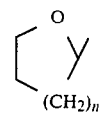

(wherein n is 1 or 2) or $R_1$ and $R_2$ represent the same phthalidyl group;

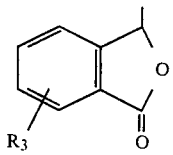

(wherein $R_3$ has the same meaning as that defined above) and provides a compound which has antitumor activity and less toxicity and can be used as a cancerocidal agent.

9 Claims, No Drawings

N-PHTHALIDYL-5-FLUOROURACILS

TECHNICAL FIELD

The present invention relates to N-phthalidyl-5-fluorouracil derivatives, particularly N-phthalidyl-5-fluorouracil derivatives represented by the general formula (I)

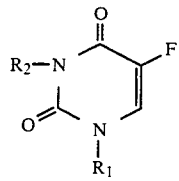

wherein one of $R_1$ and $R_2$ represents the phthalidyl group:

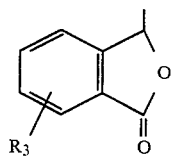

(wherein $R_3$ is a hydrogen atom, a halogen atom or a group selected from alkoxyl groups or alkyl groups) and the other represents a hydrogen atom, an acyl group or a cyclic ether group

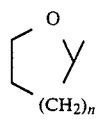

(wherein n is 1 or 2), or $R_1$ and $R_2$ represent the same phthalidyl group;

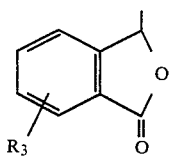

(wherein $R_3$ is the same as that defined above). The object of the present invention is to provide a substance which has an excellent antitumor activity and can be used as a cancerocidal agent.

BACKGROUND TECHNOLOGY

Heretofore, 5-fluorouracil and various derivatives thereof have been known as antitumor agents. However, all of these derivatives do not always show the effectiveness expected and it has been generally recognized that they cause immunosuppression when used. In addition, some of 5-fluorouracil derivatives are highly toxic and might have side effects.

Consequently, the present invention aims to provide compounds which have no defect shown by conventional 5-fluorouracil derivatives, have less toxicity, can be dissolved in an oily material in a stable state so that they can be easily absorbed in body and are useful as cancerocidal agents.

DISCLOSURE OF THE INVENTION

The present invention relates to N-phthalidyl-5-fluorouracil derivatives (compounds).

The compounds provided according to the general formula (I) in the present invention are N-phthalidyl-5-fluorouracil derivatives represented, for example, by the general formulae (II) and (III)

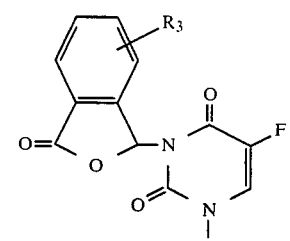 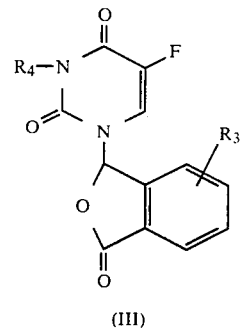

wherein $R_4$ represents a hydrogen atom, an acyl group, a cyclic ether group

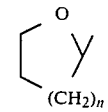

(wherein n is 1 or 2) or a phthalidyl group

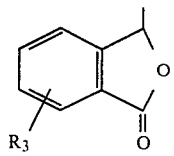

(wherein $R_3$ is a hydrogen atom, a halogen atom or a group selected from alkoxyl groups or alkyl groups). In this case, the substitution position of $R_3$ in the phthalidyl group;

is not particularly limited and one or more of the same may be substituted at the position 4, 5, 6 or 7 of the group, respectively. The "acyl group" used in the present specification means lower alkanoyl group having 1-6 carbon atoms, benzoyl group or substituted benzoyl group, more concretely, formyl, acetyl, propionyl, butyryl, benzoyl, toluyl, methoxybenzoyl, chlorobenzoyl group or the like. The "alkyl group" means straight chain or branched alkyl group having 1-6 carbon atoms, for example, straight chain or branched alkyl group in such a group as methyl, ethyl, propyl, butyl, amyl or hexyl group, etc., respectively. Further, "alkoxyl group" means alkoxyl group corresponding to the alkyl group mentioned above.

N-phthalidyl-5-fluorouracil derivatives represented by the general formula (I) in the present invention can be prepared according to the process mentioned below.

A compound wherein $R_4$ in the general formula (II) is a hydrogen atom can be obtained by allowing 5-fluorouracil to react with a halogenated phthalide compound represented by the general formula (IV)

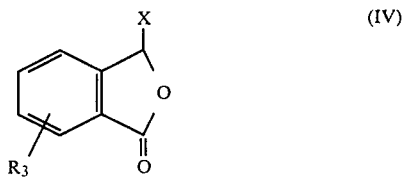

(wherein $R_3$ is the same as that defined above and X represents a halogen atom) or by the hydrolysis of a compound having an acyl group as $R_4$ in the general formula (II) obtained by allowing $N_1$-acyl-5-fluorouracil to react with a halogenated compound represented by the general formula (IV) mentioned above. This phthalidylation reaction is carried out in an appropriate solvent in the presence of a base. Such a solvent can be freely selected as far as it has no direct effect on the reaction, for instance, there can be illustrated dimethylformamide, dimethylacetamide, dimethyl sulfoxide and the like. As the base used, there can be illustrated sodium carbonate, potassium carbonate, sodium hydride, sodium amide, sodium alcoholate and the like. Further, the hydrolysis of the compound having an acyl group as $R_4$ in the general formula (II) can be carried out with water or an alcohol such as methanol, ethanol or isopropanol. In this case, as an acid catalyst, there may be added thereto an inorganic acid such as hydrochloric acid or sulfuric acid or an organic acid such as formic acid, acetic acid or propionic acid.

In order to obtain a compound having hydrogen atom or phthalidyl group as $R_4$ in the general formula (III), in the phthalidylation reaction of 5-fluorouracil mentioned above, an excess amount of a halogenated phthalide compound represented by the general formula (IV) (for instance, 2 molar ratio or more thereof to 5-fluorouracil) may be allowed to react in the presence of a relatively strong base such as sodium hydride. As another process for the preparation of $N_1$, $N_3$-diphthalidyl-5-fluorouracil, there can be used a process wherein an N-monophthalidyl compound having a hydrogen atom as $R_4$ in the general formulae (II) and (III) is further phthalidylated.

A compound having an other substituted group, for example, an acyl group as $R_4$ in the general formula (II) or (III) can be obtained by the acylation of a compound having a hydrogen atom as $R_4$ in the corresponding general formula (II) or (III), respectively, or by allowing a corresponding $N_1$- or $N_3$-acyl-5-fluorouracil compound to react with a halogenated phthalide compound represented by the general formula (IV). In this case, the acylation may be carried out by the reaction with the corresponding acyl halide or acid anhydride and, as such a reactive compound, there can be illustrated acetyl chloride, propionyl chloride, toluyl chloride, benzoyl chloride, acetic anhydride or the like. Also in this reaction is preferable the coexistence of a base in the presence of a solvent which has no direct effect on the reaction. When the halogenated phthalide compound is allowed to react, conditions for the phthalidylation reaction mentioned above can be applied without any modification.

Further, a compound having a cyclic ether group;

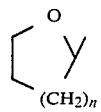

(wherein n is 1 or 2) as $R_4$ in the general formula (II) or (III) can be obtained by allowing an already known compound N-(2-tetrahydrofuranyl)- or N-(2-tetrahydropyranyl)-5-fluorouracil to react with a halogenated phthalide compound represented by the general formula (IV) under the same conditions as those for the phthalidylation reaction mentioned above, or by allowing a compound having a hydrogen atom as $R_4$ in the general formula (II) or (III) obtained according to the manufacturing process mentioned above to react with a compound represented by the general formula (V)

(wherein n is 1 or 2 and Y represents a halogen atom, an acyloxy group or a lower alkoxyl group).

Thus, N-phthalidyl-5-fluorouracil derivatives can be prepared. All of these compounds have an antitumor activity and are useful compounds as cancerocidals.

Hereafter, there are shown the results of pharmacological activity of N-phthalidyl-5-fluorouracil derivatives provided by the present invention.

<Antitumor activity>

(1) P-388 ($1 \times 10^6$ cells) was implanted in the abdominal cavity of female $BDF_1$ mice (attaining an age of 6 weeks). The test substance suspended or dissolved in a 0.3% aqueous solution of CMC was administered orally once a day for 9 days starting 1 day after the implantation and the antitumor activity was evaluated by the ratio of the survival days of the treated mice to those of the control mice. Five mice for each group were used.

(2) Meth-A ($5 \times 10^6$ cells) and MH-134 ($1 \times 10^6$ cells) were implanted subcutaneously in the side of the abdominal region of Balb/c and C3H/He mice, respectively. The test substance suspended or dissolved in a 0.3% aqueous solution of CMC was administered orally twice a day for 20 days starting 1 day after the implantation and the weight of tumor was determined after 21 days from the implantation. The antitumor activity was evaluated by the ratio of the tumor weight of the treated mice to that of the control mice. Five to six mice for each group were used. For comparison, the same procedure as that mentioned above was carried out for N-(2-tetrahydrofuranyl)-5-fluorouracil (Tegafur).

The results are shown in Table 1.

TABLE 1

| Carcinoma | Antitumor activity Activity against P-388, Meth-A and MH-134 | | | | | |
|---|---|---|---|---|---|---|
| | Compound mg/kg | Treated mice/control mice (%) | | | | |
| | | 200 | 150 | 100 | 50 | 25 |
| P-388 | Tegafur | 106$^a$ | — | 136 | 104 | 115 |

TABLE 1-continued

Antitumor activity
Activity against P-388, Meth-A and MH-134

| Carcinoma | Compound | mg/kg | Treated mice/control mice (%) | | | | |
|---|---|---|---|---|---|---|---|
| | | | 200 | 150 | 100 | 50 | 25 |
| | Compound VI | | 124[a] | — | 129 | 116 | 118 |
| | Compound VII | | 102 | — | 102 | 104 | 97 |
| | Compound VIII | | 102[a] | — | 120 | 104 | 111 |
| | Compound IX | | 111 | — | 104 | 97 | 106 |
| | Compound X | | 109 | — | 102 | 99 | 113 |
| | Compound XI | | 111 | — | 115 | 109 | 104 |
| MH-134 | Tegafur | | — | 32 | 50 | 64 | 100 |
| | Compound VI | | — | 8[a] | 22 | 34 | — |
| | Compound VIII | | — | 17 | 37 | 45 | 77 |
| Meth-A | Tegafur | | died | 23 | 44 | 65 | — |
| | Compound VI | | died | 7[a] | 26 | 50 | — |
| | Compound VIII | | 7[a] | 19 | 37 | 67 | — |

[a]Decrease of body weight was observed.

The compounds of the present invention showed excellent activities against solid tumor rather than leukemia type.

<Acute toxicity>

Ten female ICR mice attaining an age of 6–7 weeks formed a group. Each test substance was administered orally. The mortality after 3 weeks was observed and the $LD_{50}$ value was calculated therefrom. The results are as follows.

$LD_{50}$ values:
Tegafur: 1,650 mg/kg
Compound VI: 2,500 mg/kg or more
Compound VIII: 2,500 mg/kg or more <Concentration in blood>

To $BDF_1$ mice (female) attaining an age of 6 weeks was administered orally each test substance at a dose of 1 mmol/kg. Their blood was collected after definite times. After the serum was separated from the blood, it was fractionated into the unchanged substance and 5-fluorouracil which is the metabolite. Then the concentrations of 5-fluorouracil and tegafur were measured in accordance with the thin layer cup method using *Staphylococcus aureus* 209P strain, in ½ quantity of sensitive disk culture media (Eiken). The unchanged compounds VI and VIII were determined by high speed liquid chromatography. The experiment was carried out using 3–4 mice for each group.

The results are shown in Table 2 and Table 3.

TABLE 2

| Test sub-stance | Concentration of metabolite (5-fluorouracil) in blood (μg/ml) | | | | |
|---|---|---|---|---|---|
| | 0.5 | 1.0 | 2.0 | 4.0 | 7.0 hrs. |
| Tegafur | 0.33 ± 0.05 | 0.24 ± 0.01 | 0.21 ± 0.01 | 0.10 ± 0.02 | 0.06 ± 0.01 |
| Compound VI | 2.00 ± 0.14 | 1.14 ± 0.12 | 0.65 ± 0.04 | 0.14 ± 0.01 | 0.10 ± 0.01 |
| Compound VIII | 1.95 ± 0.38 | 3.55 ± 0.24 | 1.96 ± 0.23 | 0.45 ± 0.11 | 0.09 ± 0.01 |

TABLE 3

| Test sub-stance | Concentration of unchanged substance in blood (μg/ml) | | | | |
|---|---|---|---|---|---|
| | 0.5 | 1.0 | 2.0 | 4.0 | 7.0 hrs. |
| Tegafur | 232.5 ± 37.5 | 245 ± 25.0 | 190 ± 10.0 | 70.3 ± 6.3 | 0.5 ± 12.5 |
| Compound VI | 5.0 ± 0.3 | 4.1 ± 0.2 | 2.3 ± 0.3 | 0.5 ± 0.1 | 0.5 ± 0.1 |
| Compound VIII | 92.5 ± 5.8 | 162.5 ± 10.6 | 11.3 ± 9.3 | 35.5 ± 4.8 | 5.3 ± 1.9 |

The best form to practice the invention

In order to describe the present invention in more detail, it will be explained with practical examples hereinbelow.

<Example 1>

$N_1$-phthalidyl-5-fluorouracil (VI) and $N_1,N_3$-diphthalidyl-5-fluorouracil (VII)

In 10 ml of DMF were dissolved 1.30 g of 5-fluorouracil and 0.80 g of sodium hydride (60% content) was added to the stirred solution mentioned above under ice cooling. Then a solution of 4.69 g of 3-bromophthalide in 5 ml of DMF was added dropwise to the mixture. After completion of dropwise addition, the mixture was stirred for 15 minutes under ice cooling and further for 3 hours at room temperature. Then 100 ml of water was added to the mixture and the mixture was extracted with chloroform. The chloroform layer was washed with water, and dried over anhydrous sodium sulfate and then, the solvent was distilled off. The residue was washed twice with 50 ml of n-hexane and 20 ml of chloroform was added thereto. The crystal deposited was collected by filtration to obtain 0.26 g (10%) of colorless crystal of $N_1$-phthalidyl-5-fluorouracil (VI). This was recrystallized from methanol-ethyl acetate and there was obtained colorless needles having a melting point of 292°–296° (decomposed).

IR spectra: $cm^{-1}$ (KBr) 1790, 1700 and 1660 (C=O and C=C)

NMR spectra: δ(CDCl$_3$+d$_6$-DMSO) 7.43–8.17 (6H, m, Ar—H and Ar—C$\underline{H}$)

Then, the mother liquor obtained after the removal of $N_1$-phthalidyl-5-fluorouracil (VI) mentioned above was subjected to silica gel column chromatography to obtain $N_1,N_3$-diphthalidyl-5-fluorouracil (VII). That is, one of diastereomers was obtained from the first chloroform eluate. This was recrystallized from ethyl acetate to obtain 0.23 g (6%) of colorless granules having a melting point of 255°–258°.

IR spectra: $cm^{-1}$ (KBr) 1785, 1730, 1690 and 1670 (C=O and C=C)

NMR spectra: δ(CDCl$_3$+d$_6$-DMSO) 7.00 (1H, d, J=6 Hz, 6—H) 7.43–8.20 (10H, m, Ar—H and Ar—C$\underline{H}$)

From the next chloroform eluate there was obtained 2.53 g (64%) of diastereomer mixture. From the subsequent eluate there was obtained the other diasastereomer, which was recrystallized from ethyl acetate to obtain 0.28 g (7%) of colorless powder having a melting point of 249°–252°. The total yield of $N_1,N_3$-diphthalidyl-5-fluorouracil (VII) was 3.04 g (77%).

IR spectra: $cm^{-1}$ (KBr) 1770, 1730 and 1680 (C=O and C=C)

NMR spectra: δ(CDCl$_3$+d$_6$-DMSO) 6.95 (1H, d, J=6 Hz, 6—H) 7.40–8.27 (10H, m, ArH and Ar—C$\underline{H}$)

<EXAMPLE 2>

$N_3$-phthalidyl-5-fluorouracil (VIII)

(i) In 8 ml of DMF was dissolved 3.44 g of 1-acetyl-5-fluorouracil and 0.80 g of sodium hydride (60% content) was added to the stirred solution mentioned above under ice cooling. Then, a solution of 4.69 g of 3-bromophthalide in 7 ml of DMF was added dropwise to the mixture. After completion of the dropwise addition, the mixture was stirred for 3.5 hours at room temperature. Then, 100 ml of water was added to the mixture and the mixture was extracted with chloroform. The chloroform layer was washed with water and dried over anhydrous sodium sulfate and then, the solvent was distilled off. The residue was washed twice with 25 ml each of n-hexane to obtain crude $N_1$-acetyl-$N_3$-phthalidyl-5-fluorouracil. To this product were added 50 ml of 0.05N hydrochloric acid and 50 ml of ethanol and the mixture was refluxed for 15 minutes. After the solvent was distilled off, water was added to the residue and the colorless crystal produced was collected by filtration. After washing with water and drying, the product was heated with 15 ml of chloroform under reflux for 3 minutes. After filtration while hot, there was obtained 2.65 g (50%) of colorless crystal. This was recrystallized from methanol to obtain colorless needles having a melting point of 234°–237°.

IR spectra: $cm^{-1}$ (KBr) 1780, 1725 and 1675 (C=O and C=C)

NMR spectra: $\delta(CDCl_3+d_6\text{-}DMSO)$ 7.38-8.05 (m, 6H, Ar—H and Ar—C$\underline{H}$)

(ii) A mixture of 0.65 g of 5-fluorouracil, 1.17 g of 3-bromophthalide, 1.00 g of potassium carbonate and 40 ml of DMF was stirred at 100°–110° for 1.5 hours. Then, the solvent was distilled off at a reduced pressure. Water was added to the residue and the product was extracted with ethyl acetate. The ethyl acetate layer was washed with water, and dried over anhydrous sodium sulfate, and the solvent was distilled off. The residue was recrystallized from methanol to obtain 0.29 g (22%) of colorless needles having a melting point of 234°–237°. This product was completely identical with (VIII) obtained in (i) in IR spectra, NMR spectra and thin layer chromatography.

<EXAMPLE 3>

$N_1$-acetyl-$N_3$-phthalidyl-5-fluorouracil (IX)

(i) A mixture of 1.31 g of $N_3$-phthalidyl-5-fluorouracil, 5 ml of acetic anhydride and 0.25 ml of pyridine was stirred at room temperature for 30 minutes. Then, the mixture was poured into 100 ml of ice-water, and stirred vigorously for 3 minutes. The crystal was collected by filtration, washed with water, dried and then recrystallized from ethyl acetate to obtain 1.10 g (72%) of colorless granules having a melting point of 187°–190°.

IR spectra: $cm^{-1}$ (KBr) 1775, 1750, 1725 and 1690 (C=O and C=C)

NMR spectra: $\delta(CDCl_3+d_6\text{-}DMSO)$ 2.65 (3H, s, COCH$_3$) 7.45-8.18 (5H, m, Ar—H and Ar—C$\underline{H}$) 8.41 (1H, d, J=7 Hz, 6—H)

(ii) The product obtained by the phthalidylation reaction in (i) of Example 2 was recrystallized from ethyl acetate to obtain colorless crystal having a melting point of 187°–190°. This product was perfectly identical with (IX) obtained in (i) in IR spectra, NMR spectra, thin layer chromatography, etc.

<EXAMPLE 4>

$N_1$-phthalidyl-$N_3$-(o-toluyl)-5-fluorouracil (X)

(i) A mixture of 1.22 g of $N_3$-(o-toluyl)-5-fluorouracil, 1.17 g of 3-bromophthalide, 1.00 g of potassium carbonate and 10 ml of DMF was stirred at room temperature for 1 hour. Then, the solvent was distilled off at a reduced pressure. After 50 ml of water was added to the residue, the product was extracted with chloroform. The chloroform layer was washed with water, and dried over anhydrous sodium sulfate, and then the solvent was distilled off. When 30 ml of ether was added to the residue, there was obtained 1.43 g (75%) of light brown crystal. This was recrystallized from ethyl acetate to obtain colorless powder having a melting point of 199°–202°.

IR spectra: $cm^{-1}$ (KBr) 1780, 1745, 1710, 1680 and 1660 (C=O and C=C)

NMR spectra: $\delta(CDCl_3)$ 2.72 (3H, s, CH$_3$) 6.70 (1H, d, J=6 Hz, 6—H) 7.17-8.33 (9H, m, Ar—H and Ar—C$\underline{H}$)

(ii) In 20 ml of dioxane was dissolved 0.26 g of $N_1$-phthalidyl-5-fluorouracil. After 0.19 g of o-toluyl chloride was added to the stirred solution at 0°–5° C., 0.11 g of triethylamine was added dropwise to the mixture. After completion of the dropwise addition, the mixture was stirred for 2 hours at 0°–5° C. Then, the solvent was distilled off. The residue was washed with n-hexane and recrystallized from ethyl acetate to obtain 0.17 g (45%) of colorless amorphous powders having a melting point of 199°–202°. This product was perfectly identical with (X) obtained in (i) in IR spectra, NMR spectra and thin layer chromatography.

<EXAMPLE 5>

$N_3$-phthalidyl-$N_1$-(2-tetrahydrofuranyl)-5-fluorouracil (XI)

(i) In 2 ml of DMF was dissolved 1.00 g of $N_1$-(2-tetrahydrofuranyl)-5-fluorouracil. After 0.20 g of sodium hydride (60% content) was added to the solution under ice cooling, a solution of 1.17 g of 3-bromophthalide in 3 ml of DMF was added dropwise thereto. After the completion of dropwise addition, the mixture was stirred at room temperature for 4 hours. To the reaction mixture produced was added 50 ml of water and the resultant mixture was extracted with chloroform. The chloroform layer was washed with water, and was dried over anhydrous sodium sulfate, and then the solvent was distilled off. The residue was washed twice with 25 ml each of n-hexane and subjected to silica gel column chromatography. A colorless oily substance obtained from chloroform eluate was solidified on trituration with a small amount of ethyl acetate. The yield was 1.22 g (74%). This was recrystallized from ethyl acetate to obtain colorless granules having a melting point of 154°–157°.

IR spectra: $cm^{-1}$ (KBr) 1765, 1715 and 1660 (C=O and C=C)

NMR spectra: $\delta(CDCl_3)$ 1.52-2.58 (4H, m, 3' and 4'—CH$_2$—) 3.72-4.52 (2H, m, 5'—CH$_2$) 5.72-6.12 (1H, m, 2'—H) 7.32-8.15 (6H, m, 6—H, Ar—H and Ar—C$\underline{H}$)

(ii) A mixture of 2.02 g of $N_3$-phthalidyl-5-fluorouracil, 1.68 g of 2-t-butyloxytetrahydrofuran and 5 ml of DMF was stirred at 150°–165° C. for 5 hours. Then, DMF and excess 2-t-butyloxytetrahydrofuran were distilled off. To the residue was added water and the mixture was extracted with chloroform. The chloroform layer was washed with water. The extract was dried over anhydrous sodium sulfate and then, the solvent was distilled off. The residue was subjected to silica gel column chromatography wherein chloroform was an eluate to obtain 1.56 g (61%) of colorless oily substance. This was crystallized from ethyl acetate to obtain colorless granules having a melting point of 154°–157°. This product was perfectly identical with (XI) obtained in (i) in IR spectra, NMR spectra and thin layer chromatography.

<EXAMPLE 6>

$N_1$-phthalidyl-5-fluorouracil (VI)

In 5 ml of DMF was dissolved 4.68 g of $N_3$-benzoyl-5-fluorouracil and 0.80 g of sodium hydride (60% content) was added to the stirred solution under ice cooling. Then, a solution of 4.67 g of 3-bromophthalide in 10 ml of DMF was added dropwise to the mixture. After the completion of the dropwise addition, the mixture was stirred under ice cooling for 15 minutes and further for 1 hour at room temperature. The reaction mixture produced was poured into 200 ml of water and the mixture was extracted with chloroform. The organic layer was washed with water and dried over anhydrous sodium sulfate. Then, the solvent was distilled off and the residue was washed with petroleum ether. The crystal obtained was recrystallized from ethyl acetate to obtain 3.63 g (50%) of colorless powder having a melting point of 207°–210°. The mother liquor was subjected to silica gel column chromatography to obtain 0.67 g (9%) of crystal. Thus, there was obtained totally 4.30 g (59%) of $N_3$-benzoyl-$N_1$-phthalidyl-5-fluorouracil.

IR spectra: cm$^{-1}$ (KBr) 1780, 1750, 1710, 1680 and 1660 (C=O and C=C)

NMR spectra: δ(CDCl$_3$) 6.85 (1H, d, J=6 Hz, 6—H) 7.43–8.26 (10H, m, Ar—H and Ar—CH)

Then, a mixture of 3.0 g of the compound mentioned above, 450 ml of ethanol and 25 ml of acetic acid was heated under reflux for 35 hours. The colorless crystal which precipitated on cooling was collected by filtration and was washed with ether to obtain 0.69 g of $N_1$-phthalidyl-5-fluorouracil (VI). Further, 0.48 g of the same was obtained from the mother liquor. Total yield was 1.07 g (54%). This was recrystallized from methanol-ethyl acetate to obtain colorless needles having a melting point of 292°–296° (decomposed). This product was perfectly identical with (VI) obtained in Example 1 in IR spectra, NMR spectra and thin layer chromatography.

We claim:

1. A N-phthalidyl-5-fluorouracil compound represented by the formula (I):

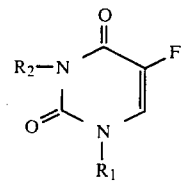

wherein one of $R_1$ and $R_2$ represents the phthalidyl group:

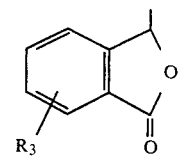

wherein $R_3$ represents a hydrogen atom and the other of $R_1$ and $R_2$ represents a hydrogen atom, an acyl group or a cyclic ether group:

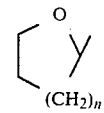

wherein n is 1 or 2, said acyl group being selected from the group consisting of a $C_{1-6}$ alkanoyl group, a benzoyl group and a benzoyl group substituted on one position of the benzene ring with a substituent selected from the group consisting of a $C_{1-6}$ alkyl group, a $C_{1-6}$ alkoxyl group and a halogen atom; or $R_1$ and $R_2$ represent the same phthalidyl group heretofore defined wherein $R_3$ has the same meaning defined above.

2. A N-phthalidyl-5-fluorouracil compound according to claim 1, wherein said substituent on the benzene ring of the benzoyl group is selected from the group consisting of a methyl group, a methoxyl group and a chlorine atom.

3. A N-phthalidyl-5-fluorouracil compound according to claim 1; namely, $N_1$-phthalidyl-5-fluorouracil.

4. A N-phthalidyl-5-fluorouracil compound according to claim 1; namely, $N_1,N_3$-diphthalidyl-5-fluorouracil.

5. A N-phthalidyl-5-fluorouracil compound according to claim 1; namely, $N_3$-phthalidyl-5-fluorouracil.

6. A N-phthalidyl-5-fluorouracil compound according to claim 1; namely, $N_1$-acetyl-$N_3$-phthalidyl-5-fluorouracil.

7. A N-phthalidyl-5-fluorouracil compound according to claim 1; namely, $N_1$-phthalidyl-$N_3$-(o-toluyl)-5-fluorouracil.

8. A N-phthalidyl-5-fluorouracil compound according to claim 1; namely, $N_3$-phthalidyl-$N_1$-(2-tetrahydrofuranyl)-5-fluorouracil.

9. A N-phthalidyl-5-fluorouracil compound according to claim 1; namely, $N_1$-phthalidyl-$N_3$-benzoyl-5-fluorouracil.

* * * * *